United States Patent
Heck et al.

(10) Patent No.: US 9,999,443 B2
(45) Date of Patent: Jun. 19, 2018

(54) INSTRUMENT HEAD SINGLE LOADER

(71) Applicants: Sandy Lawrence Heck, Los Angeles, CA (US); Eric William Conley, South Berwick, ME (US); Ricardo Alexander Gomez, Lighthouse Point, FL (US)

(72) Inventors: Sandy Lawrence Heck, Los Angeles, CA (US); Eric William Conley, South Berwick, ME (US); Ricardo Alexander Gomez, Lighthouse Point, FL (US)

(73) Assignee: INNERSPACE SURGICAL CORPORATION, Pompano Beach, FL (US)

( * ) Notice: Subject to any disclaimer, the term of this patent is extended or adjusted under 35 U.S.C. 154(b) by 0 days. days.

(21) Appl. No.: 15/380,025

(22) Filed: Dec. 15, 2016

(65) Prior Publication Data

US 2017/0172621 A1 Jun. 22, 2017

Related U.S. Application Data

(60) Provisional application No. 62/269,512, filed on Dec. 18, 2015.

(51) Int. Cl.
*A61B 17/34* (2006.01)
*A61M 13/00* (2006.01)
(Continued)

(52) U.S. Cl.
CPC ........ *A61B 17/3423* (2013.01); *A61B 1/3132* (2013.01); *A61B 17/29* (2013.01);
(Continued)

(58) Field of Classification Search
CPC ... A61B 17/3423; A61B 17/29; A61B 1/3132; A61B 2017/00336; A61B 2017/00362;
(Continued)

(56) References Cited

U.S. PATENT DOCUMENTS 5,766,196 A * 6/1998 Griffiths ................. A61B 17/29
600/564
7,481,793 B2 * 1/2009 Abrams ............ A61M 25/0662
604/164.01
(Continued)

*Primary Examiner* — Pedro Philogene
*Assistant Examiner* — David C Comstock
(74) *Attorney, Agent, or Firm* — Grogan, Tuccillo & Vanderleeden, LLP

(57) ABSTRACT

A single instrument head loading device for use in needlescopic surgery comprises a shaft having maneuverable structure on a proximal end for use in correctly positioning an instrument head at a distal end thereof through manipulation of at least one wire engaged to a distal end loader within which the instrument head is held by maneuvering the maneuverable structure at the proximal end, to which a proximal end of the at least one wire is attached, the at least one wire traversing the length of the shaft and the distal end loader being positioned in a suitable position allowing engagement of the instrument head under continuous direct visualization to a distal end of a cooperating shaft of a surgical instrument as well as allowing for disengagement of the instrument head back into the distal end loader under continuous direct visualization, the engagement and disengagement taking place within a body cavity.

21 Claims, 11 Drawing Sheets

(51) Int. Cl.
 *A61B 1/313* (2006.01)
 *A61B 17/29* (2006.01)
 *A61B 17/00* (2006.01)

(52) U.S. Cl.
 CPC . *A61M 13/003* (2013.01); *A61B 2017/00336* (2013.01); *A61B 2017/00362* (2013.01); *A61B 2017/00455* (2013.01); *A61B 2017/00473* (2013.01); *A61B 2017/2931* (2013.01); *A61M 2202/0007* (2013.01); *A61M 2202/02* (2013.01)

(58) Field of Classification Search
 CPC ........... A61B 2017/00455; A61B 2017/00473; A61B 2017/2931; A61M 13/003; A61M 2202/0007; A61M 2202/02
 USPC ......................................................... 600/204
 See application file for complete search history.

(56) References Cited

U.S. PATENT DOCUMENTS

| | | | | |
|---|---|---|---|---|
| 2003/0225364 | A1* | 12/2003 | Kraft | A61B 10/025 604/35 |
| 2006/0063965 | A1* | 3/2006 | Aboul-Hosn | A61M 25/0043 600/16 |
| 2009/0131950 | A1* | 5/2009 | Liu | A61B 17/8811 606/94 |
| 2010/0016883 | A1* | 1/2010 | Christoudias | A61B 17/29 606/205 |
| 2014/0018732 | A1* | 1/2014 | Bagaoisan | A61M 25/0136 604/95.04 |

* cited by examiner

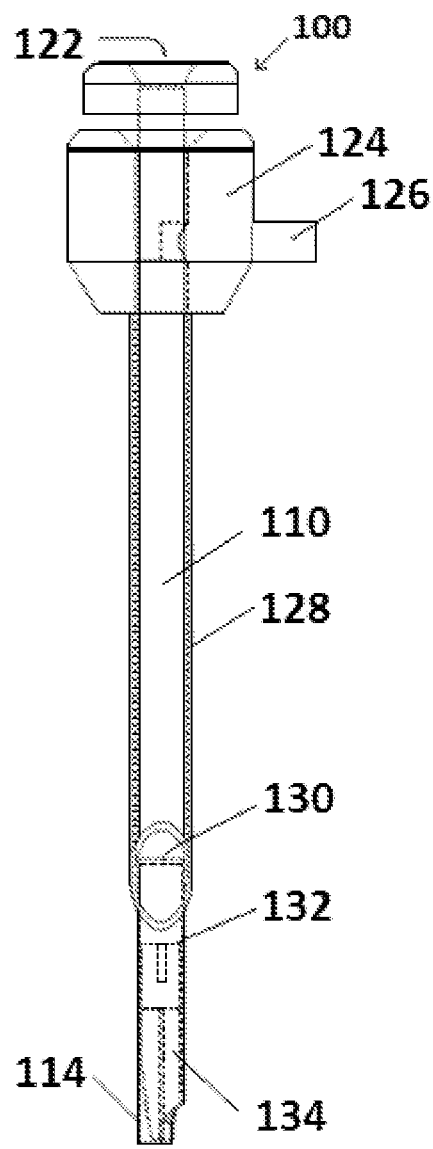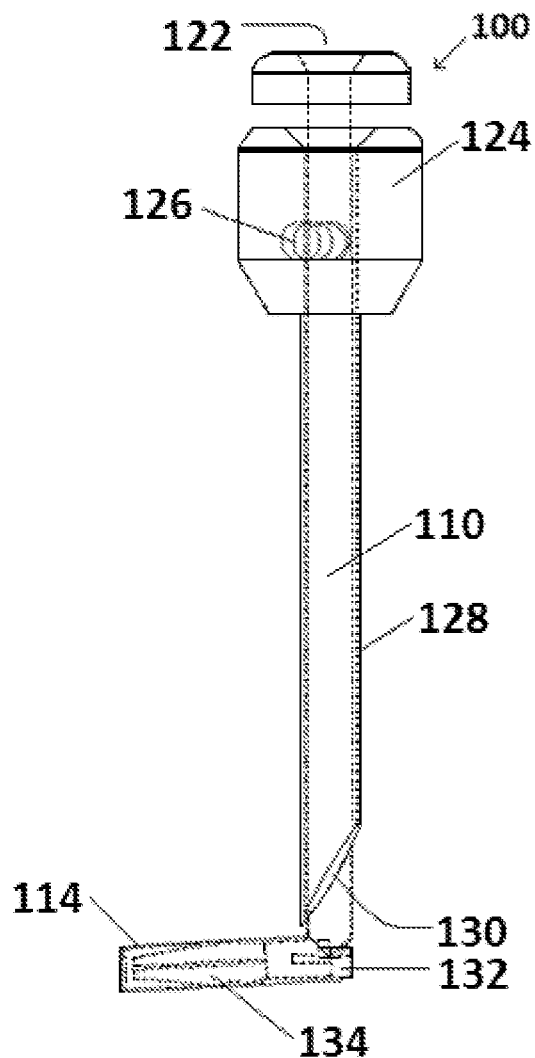
Figure. 2A                    Figure. 2B

INSTRUMENT HEAD SINGLE LOADER

CROSS REFERENCE TO RELATED APPLICATIONS

This application claims priority to U.S. Provisional Application Ser. No. 62/269,512, filed on Dec. 18, 2015 and entitled Laparoscopic Instrument Head Single Loader, which is hereby incorporated by reference herein in its entirety.

FIELD OF INVENTION

The present application is directed toward medical instruments and, more particularly, to a specialized instrument head insertion device whereby attachment and detachment can take place under direct visualisation.

BACKGROUND OF INVENTION

Laparoscopy is a surgical procedure performed through small incisions in the abdomen whereby a trocar/cannula device is inserted to provide a means for passage of medical instruments. A thin cylindrical instrument called a laparoscope, connected to a camera, is then used to provide a clear picture of the abdominal cavity to the surgeon.

Prior to starting a surgical procedure, a small incision is performed on the abdominal wall of the patient whereby a trocar/cannula device is inserted. Trocar device diameters range in size from 5 to 12 mm and provide a clear passage for the introduction of medical devices into the abdomen. A device called an insufflator is then used to inflate the abdominal cavity area with a gas such as carbon dioxide, creating space. Once the abdominal opening is secured, a special medical viewing device called a laparoscope is inserted thru the trocar opening permitting the surgeon to view the abdominal cavity space. Typically, several additional incisions are made ranging in size from 5-12 mm for the introduction of other medical devices.

The origins of the word Laparoscope can be traced back to the Greek word for "Laparo" meaning "flank". A flank is the side of the body between the ribs and hips commonly referred to as the abdomen and the word "scope" meaning to look at or examine. Hence Laparoscopes provide a means of looking inside the abdomen of a person.

The first use of a Laparoscope goes as far back as 400 BC where the physician Hippocrates (460-377 BC) mentioned the use of a device called a rectoscope. Its use was for inspecting the oral cavity and pharynx of a person. When a tool is used to view the interior of a person thru a natural opening of the body such as the mouth or nose it is more accurately referred to as an endoscope. Laparoscopes and Endoscopes have permitted tremendous strides in the medical field.

It wasn't until 1805 that a physician named Phillip Bozzini of Mainz, Germany invented the Lichtleiter, also referred to as the Bozzini Endoscope. The Lichtleiter consisted of two parts, (1) a light container with an optical part and (2) a mechanical part which consisted of viewing channels adapted to fit inside a body. The Lichtleiter was a channel constructed of various attachments that used concave lenses whereby half of the channel transmitted the light from a candle to the tip of the device and the other half of the opening returned the reflected light showing the surgeon the interior view of the patient. The candle with angled mirrors inside the device provided the light that enabled the physician to see the abdominal cavity. This approach was not practical because of its limitations of maintaining a heated light source, but it was the predecessor of today's laparoscopes and at the time the first device to inspect the interior of a human body.

Laparoscopy continued to evolve. In 1901 a Doctor by the name of George Kelling performed the first examination of an abdominal cavity (in a dog) by inflating the cavity with gas and then inserting an endoscope. He is often credited with introducing the field of Laparoscopy. In 1910 Victor Elner used a gastroscope to view the interior of a stomach and shortly thereafter a flexible gastroscopy was designed. Thereafter, in 1911. the first Laparoscopy was performed on a human by the Swedish Doctor H. C. Jacobeus. In spite of the technical advances that were being made, problems persisted with the heat produced at the tip of the scope when a flame was used for lighting and visualization problems such as blind spots in the field of view. These problems limited the use of Laparoscopy. Its main purpose remained diagnostic.

In the early 20th century with the invention of the light bulb and electrical devices by Thomas Edison, significant advances began taking place. Small light sources could now be attached to the distal tip of Laparoscopes without the need for cooling. The next great evolution happened in the 1950's when significant advances took place in the field of fiber optics. Fiber Optics provided great flexibility and the introduction of even smaller light sources into the abdomen without burning the patient.

As surgeries kept evolving, limited interest was focused on minimally invasive type surgeries. It was believed that larger incisions were better. However as some of the many advantages of minimal invasive surgery became apparent such as lower operating cost, less patient trauma, less scarring, less pain, lower surgical complications, quicker recovery times, shortened hospital stays, and less chance of infection, a need developed to find therapeutic uses for Laparoscopy. In the 1970s, thanks to Gynecologists and Gastroenterologists, the use of Laparoscopy began changing from diagnostic to therapeutic uses.

The development of very small high-resolution television cameras and CCD (charged coupled devices) tremendously propelled advances in therapeutic uses. As problems presented themselves inventors focused on solutions that kept Laparoscopic surgeries moving forward. An example of how a problem in laparoscopy led to a great solution is the problem of fogging and visualization that developed in surgery. Inventors such as Ricardo Alexander Gomez, Sandy Lawrence Heck, and Eric Conley developed and patented a revolutionary method for maintaining laparoscopic lenses crystal clear during procedures and dramatically improved the visualization and effectiveness for these types of surgeries with the use of a device called a D-Help®.

As the field of minimally invasive surgery continues evolving less invasive techniques are desired. The need for smaller laparoscopic tools has also developed. A newer version of laparoscopy has evolved called needlescopic surgery. Needlescopic surgery is a progression of laparoscopic surgery whereby incisions smaller than 3 millimeters are made. Virtually no scarring occurs, pain is reduced, and recovery times are faster. However, the problem associated with this new type of procedure is the limited functionality of the insertion instrument. As the instruments became thinner, the heads of the instruments became smaller and less effective to manipulate tissues and organs. For this reason, among others, needlescopic surgery is not functional for most procedures and has not been widely adopted by the surgical community.

Another new type of surgery called Single Incision Laparoscopic Surgery (SILS) has also been tried to reduce the number of incisions related to surgery. The concept is that a single incision is made at the umbilicus allowing a specialized tool to be placed at the opening. The opening allows the insertion of several very small instrument tools into the abdomen. The problems associated with this procedure are first in the level of complexity for each procedure versus the traditional laparoscopic procedure, the lack of functionality of the smaller tools, and the very tight working area. It is usually limited to only 3 very small instrument devices which often lack the full functionality required by traditional surgeons.

Another new type of surgery used today is called (NOTES) Natural Orifice Transluminal Endoscopic Surgery. It basically involves placing a flexible endoscope through one of the body's natural orifices, like the mouth, anus, vagina, or urethra. Its purpose is to achieve access to a space near the affected area. Some of the problems associated with this type of surgery are that the number of instrument heads used is usually limited to only one, not all areas of the body are accessible, and since most views are two dimensional there are special orientation problems.

An additional problem associated with both Single Incision Laparoscopic Surgery (SILS) and Natural Orifice Transluminal Endoscopic Surgery (NOTES) are their lack of ability to achieve triangulation. Triangulation in this instance can be defined as the ability to come at a target from different directions or angles. Triangulation provides significant benefits to the surgeon, among them are: effective control of the surgical procedure and the ability to better manipulate internal body parts. When this ability is lost, it is difficult to effectively perform these types of surgeries. This is one of the reasons that have prevented SILS and NOTES from being widely adapted. Our Technology solves this problem by facilitating triangulation from many directions, a feature that is both lost in SILS and NOTES.

People have experimented with the concept of attaching larger instrument heads to thin shafts inside the body, but no effective method has been developed or invented to facilitate the insertion and attachment of such instrument heads within the body especially under direct visualization.

In laparoscopic surgery, incisions are made ranging from 5-12 mm and usually requiring up to 4 separate incisions. In the specialized field of needlescopic surgery the instrument heads are often too small and lack functionality. Visualization of the attachment process is also a problem that has limited the internal attachment process to an external one. The challenge has been in finding a means of inserting, removing and remotely attaching a normal sized medical instrument head inside the abdomen of a patient. The benefits are numerous to the patient including reduced scarring, quicker recovery times, less chance of infections, and lower morbidity risks associated with infections. The advantages to the surgeon are better handling, and better functionality of the instrument heads, often a tradeoff that is associated with smaller instrument heads.

As newer technologies continue to evolve, there is a need in the field for smaller tools having better rigidity and strength characteristics. In U.S. Patent Application Ser. No. 62/093,789, filed on Dec. 18, 2014, entitled "Method and Apparatus for Securing Laparoscopic Instrument Heads in the Abdomen Under Direct Visualization", by same Inventors, a new technology is introduced whereby thin shafts having diameters measuring between 1-4 mm are introduced.

As elongated instruments continue to reduce in diameter, their rigidity comes into question. The further they are extended the weaker they become. Additionally, as thinner tools are used the means of attaching them securely to instrument heads are also needed.

These and other aspects, features and advantages of the present invention will become more readily apparent from the attached drawings and the detailed description of the preferred embodiments which follow.

SUMMARY OF INVENTION

The field of Surgery has continued to evolve initially from large insitions leaving large scars, longer recovery times, higher propensity for infections and longer recovery times, to smaller insitions, less scaring, less infections and quicker recovery times. As a result of this, a need in the field has evolved requiring smaller specialized instruments and techniques for these new procedures.

The current invention is directed towards new tools and methods for performing minimally invasive surgery whereby insitions necessary to insert a medical instrument usually measuring between 10-15 mm are now made between 2-3 millimeters. As a result of this, smaller medical instrument devices are used employing a specialized method of attaching the medical instrument head to a shaft.

Initially a Trocar/Cannula device is used to pierce the skin where the umbilical scar is located. The Trocar/Cannula device is an air tight self sealing device that permits inflation by an inert gas to abdominal cavity of a patient. An inert gas is then pumped into the abdominal cavity of a patient creating space for the surgeon to maneuver. At this point a specialized insertion tool is introduced into the cannula passageway. This insertion tool introduces a single instrument head into the abdomen of the patient and once reaching the end of the cannula passageway immediately tilts not limited to but up to 180 degrees from its insertion orientation. A laparascope is then introduced through the upper passageway of the medical instrument insertion device. An orientation finder indicates the orientation of the instrument. The Laparascope maintains constant visualization of the instrument head throughout the attachment process.

A specialized shaft instrument is used to pierce the percutaneous surface of the abdomen. To ease in the attachment process an orientation marker can be used to indicate the proper orientation of the instrument head and allow the surgeon to perform medical procedures. The opening created is not limited to, but is between 2-4 mm in size. The distal tip of the shaft has a specialized attachment and locking feature. The shaft is directed to a medical device extending from the umbilical opening and is attached to a medical instrument head. A series of locking features are employed to safely fasten the medical head to the shaft. The medical instruments are not limited to but include Scrapers, Graspers, Maryland Dissectors, Claw Forceps, Fenestrated Grasping Forceps, Electrodes, or Tapered Grasping Forceps. It should be pointed out that the laparoscope is not permanently attached to the insertion tool; it has the freedom to move throughout the insertion tool or trocar. One of its functions is to observe the attachment/detachment of the medical instrument head to a medical attachment shaft.

The laparoscopic instrument head single loader can now be removed giving the surgeon the option of inserting several more instrument heads to correspond with the number of desired shafts inserted. This procedure is repeated per number of instrument heads used. The present invention is not limited to but in this case has one Laparoscopic Instrument Head Single Loader per instrument head used.

Once the desired medical instrument heads are attached under direct visualization the insertion tool is completely removed. The available opening can now be used for other purposes including the insertion of a laparoscope to maintain visualization of the procedure.

In an alternative embodiment a specialized memory metal wire having elasticity qualities is used. The memory metal wire used exhibits the unique properties of memory shape and elasticity. Its elasticity properties permits it to be bent into different shapes when under pressure and its metal memory characteristics allows it to freely return to its initial heat treated form when no pressure is present. In this application the metal memory wire has a distal bend that can conform to but is not limited ranges of 15-180 degrees. Its purpose is to guide and properly orient a pencap device, containing a medical instrument head. When the pencap device bends to its preheated position, it exposes the medical head attachment features used to connect and provide control to the instrument shaft device. The memory metal wire may have a control knob or handle at its proximal end, which will facilitate the insertion and orientation of the instrument head.

The insertion tool may have a series of lumen passages permitting multiple memory forming wires to be configured in an array. A tab guide(s) located at the proximal end, permits the surgeon to push, pull or turn the memory wire(s) in the delivery tube permitting it to reach the end of the trocar. The memory wire is attached to a pencap device and that holds the instrument head in place. Its purpose it to properly orient the instrument head to a pencap device. When the memory wire reaches a predetermined position outside the cannula it will automatically bend to a predetermined angle, changing the orientation of the pencap and exposing the instrument heads multi locking features. The pencap device firmly holds the medical instrument head in place protecting it against constant vibrations or strong movements When the medical instrument handle is used to pull the instrument head out it will snap out past a small circular holding barrier.

In an alternative embodiment a shepherds hook type configuration may be used. It consists of a spring steel wire with a pen cap attached in a 180 degrees opposite direction. A medical instrument head sitting tightly inside the pen cap. The medical instruments attachment feature is exposed for quick attachment. The shepherds hook consists of a knob at its proximal end extending through out its length to a 180 degree bend at its distal end where an attached a pen cap device is firmly attached. The delivery tube has a smaller lumen or paired lumen openings that are used to guide the shepherds hook. The delivery tube is inserted into the trocar, whereby the handle is used to push the shepherds hook past the opening and can be slightly retracted causing the distal end of the shepherds hook to attach to the trocar distal tip. This facilitates the engagement of the medical instrument device located inside the pencap device to the handler attachment device.

The basic procedure a surgeon would use is to first insert the medical sleeve device inside the trocar, then inserting the medical device desired into the lumen which has an opening similar to a "C". A handler is used to push it throughout the trocar opening. The distal tip is preseated through the opening to its maximum forward position causing the instrument head to be extracted. The pen cap can also be presented forward whereby the instrument head rest on the sleeve device providing a direct line of site for the laparoscopic camera.

One of the methods used is called flop loading which is achieved in two ways, one allows the user to "flip" the loaded head into position using a slide on the handle (Manual Flop). The other method uses a fixed spring wire to flip the head when it passes the end of the trocar (auto flip).

Another method used is called the slide and twist. In this method a candy cane shaped shaft with a head, is inserted into an exaggerated extruded tube, allowing the shaft to occupy the smaller lumen and the head to occupy the larger lumen. When the head is presented into the body the shaft is turned and the head swings out of the view of the camera allowing an unobstructed view of the attachment.

Today there is a need in the field for smaller and more effective laparoscopic tools, a means of providing direct visualization and methods that minimize the use of additional trocars inserted into the abdominal cavities of patients. Therefore, there is a need in the field for a means of effectively attaching and securing full-sized laparoscopic instrument heads to small diameter instrument shafts within the body while under direct visualization. This need would minimize the number and size of incisions performed for each procedure. Additionally, it is the goal of this invention to provide innovative means and techniques for inserting medical instruments devices used in needlescopic surgery that can be properly oriented for quick attachment and detachment while maintaining direct visualization throughout.

These objectives being met, as well as other aspects, features and advantages of the invention will become more readily apparent from perusal of the figures and detailed description of exemplary preferred embodiments which follow.

BRIEF DESCRIPTION OF DRAWINGS

The preferred embodiments of the invention will hereinafter be described in conjunction with the appended drawings provided to illustrate and not to limit the invention, in which:

FIG. 2A provides a side perspective view of a laparoscopic head single loader according to an alternative embodiment of the invention.

FIG. 2B provides a perspective view of the laparoscopic head single loader of FIG. 2A in a properly pivoted position, making it ready for attachment.

DETAILED DESCRIPTION OF THE PREFERRED EMBODIMENT

Figures 1A, 1B:
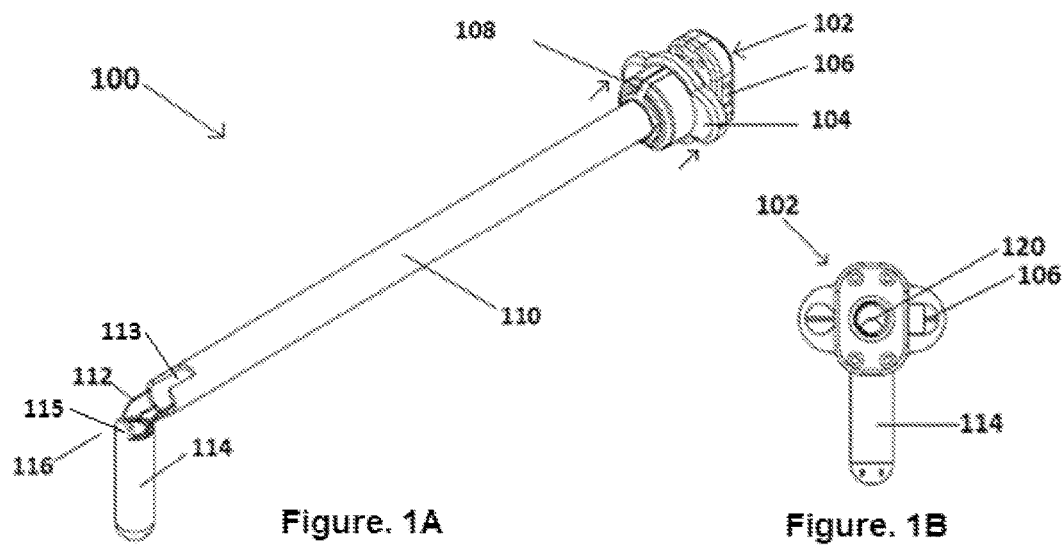
FIG. 1A provides a perspective view of a laparoscopic head single loader according to a preferred embodiment of the invention.
FIG. 1B provides a side perspective view of the laparoscopic head single loader.
Figure 1C:
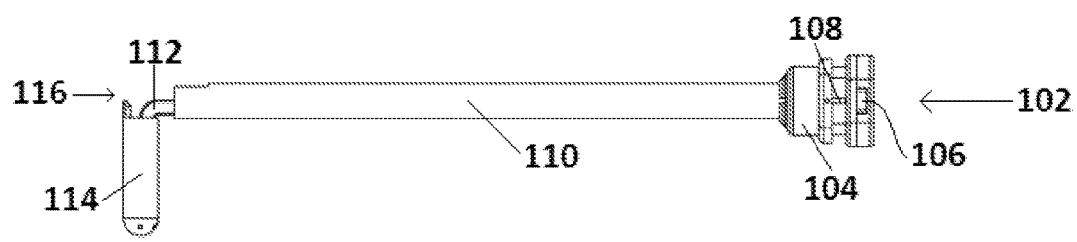
FIG. 1C provides a top perspective view of the laparoscopic head single loader, exposing the instrument attachment area.
Figure 1D:
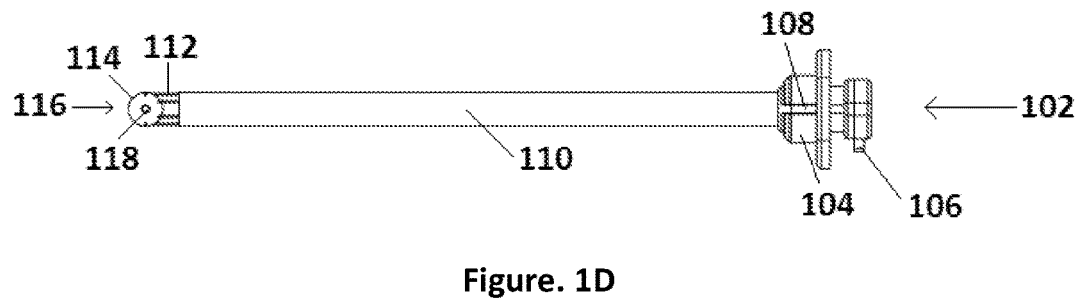
FIG. 1D provides a front perspective view of the laparoscopic head single loader.

Below are exemplary implementations provided to enable persons skilled in the art to make or use the embodiments of the disclosure and are not intended to limit the scope of the disclosure, which is defined by the claims. For purposes of description herein, the terms "upper", "lower", "left", "rear", "right", "front", "vertical", "horizontal", and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations.

Figure 3:
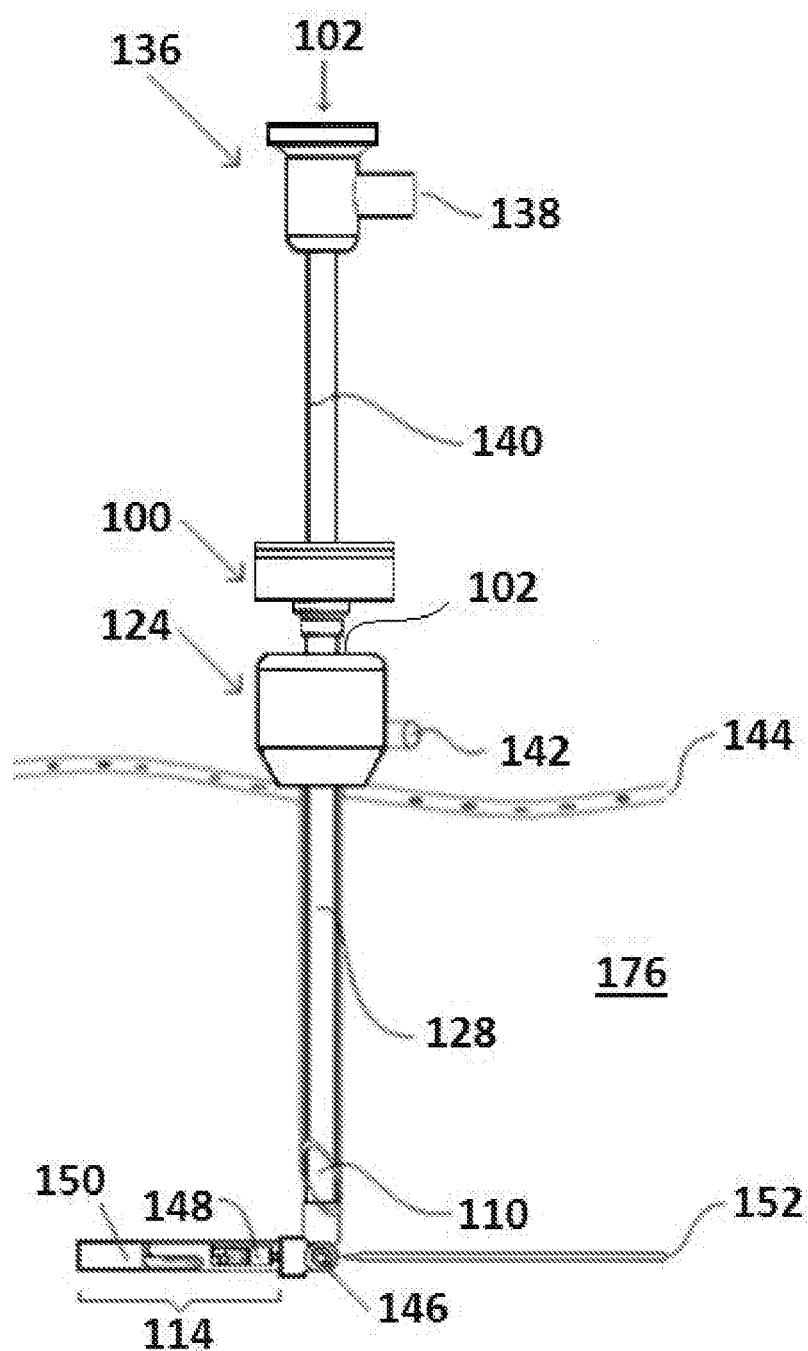
FIG. 3 provides a perspective view of the laparoscopic head single loader of FIG. 2A, shown being attached to a medical shaft device.

FIGS. 1A-1D illustrate perspective views of an exemplary laparoscopic instrument head single loader (100) having a proximal top opening (102) used for inserting a laparoscope (136 of FIG. 3). A manual pen cap straightening device handle (104) used by the surgeon by squeezing the handle (104) which is connected to a pen cap attachment wire (112) that pulls at least one wire toward the proximal end of the laparoscopic single loader device (100) and straightens the instrument pen cap device (114), which serves as a generally cylindrical housing for the instrument head (134) during insertion. At the proximal top opening of the laparoscopic single loader device (102) is a special orifice opening tab (106) that controls the opening of the air tight valve aperture (120) within the loader (100) which is used to maintain gas pressure in the patient's abdomen by only opening when the tab (106) is squeezed towards the center. Only when the air-tight valve aperture (120) is open will a laparoscope (136) be inserted. A guide channel (108) is used to maintain the proper orientation of the pen cap attachment wire (112) by providing a channel that guides the manual pen cap straightening device handle (104) in a direction longitudinal to the delivery tube (110). Delivery tube (110) has a length that permits proper insertion into the abdomen of the patient, it is not limited to a fixed length but may vary. An instrument pen cap device (114) is connected to the distal end (116) of the pen cap attachment wire (112) used for straightening the pen cap device (114) when being inserted through the delivery tube (110). With respect to FIG. 1B, a side perspective view of an air-tight valve aperture (120) is displayed in its sealed position preventing inert gas from escaping the abdomen.

In operation, an instrument head (134) for attachment to an instrument within the body of a patient can be placed within the pen cap device (114) and the wire (112) pulled to bring the pen cap device (114) into longitudinal alignment/registration with the delivery tube (110). The laparoscopic single loader device (100) is inserted through a trocar (124 FIG. 2B), and the manual pen cap straightening device handle (104) is pulled causing the pen cap attachment wire (112) to pull the instrument pen cap device (114) to a straightening position and/or maintain the pen cap device (114) in longitudinal alignment with the delivery tube (110). Once the pen cap device (114) containing the instrument head (134) is positioned within a patient, a laparoscope can be inserted through the opening (102) so that visualization of the attachment head (134) can be achieved so that attachment of the head (134) to an instrument shaft can be carried out. In particular, once inserted into a patient, the handle (104) can be released to expose the instrument head (134) and its attachment point (118), as shown in FIGS. 1A-1C and FIG. 3. In particular, when the instrument pen cap device (114) is in the proper position the instrument head attachment point (118) is properly oriented for attachment to an instrument shaft (152 FIG. 3). A pen cap tab (113) is incorporated being positioned in a suitable position with respect to delivery tube positioning tab slot (115).

With respect to FIG. 2, an alternative embodiment not having a manual pen cap straightening device handle (104) is illustrated. A proximal single loader guide (122) is incorporated, used to guide a laparoscope (136 of FIG. 3) into the delivery tube (110) for direct continuous visualization. The delivery tube (110) is inserted into the trocar (124) having a trocar air valve (126) used to maintain pressure inside the abdomen (176 of FIG. 3). The delivery tube (110) is inserted into the trocar lumen causing it to pass through the trocar distal opening (130). Once the instrument pen cap device (114) protrudes pass the trocar distal opening (130) the pen cap (114) bends, not limited to but approximately 90 degrees exposing the instrument head attachment area (132) so that an instrument shaft (152 of FIG. 3) can properly attach to the instrument head (134).

With respect to FIG. 3 a perspective view of the laparoscopic single loader device (100) is illustrated fully inserted into a patient's abdomen (176). In this embodiment, a pivot point (146) is used for tilting the instrument pen cap device (114) to the proper angle so that an instrument shaft (152) can properly attach itself to the instrument head attachment mechanism (148). The laparoscopic single loader device (100) is first fully inserted into trocar (124), the instrument pen cap device (114) tilts to the proper angle for attachment. A laparoscope (136) is then inserted into the proximal top opening of the laparoscopic single loader device (102), which is already inserted into a trocar (124), that perforates the percutaneous skin (144) of the patient. Direct continuous visualization of the attachment procedure is maintained. The instrument shaft (152) and the instrument head attachment mechanism (148) are securely engaged under direct continuous visualization. Once this procedure is completed the laparoscopic single loader device (100) can be removed permitting the laparoscope (136) to maintain visualization. Pivot point (146) provides a structure that may be preformed to a particular angle to the device structure.

Figure 4:
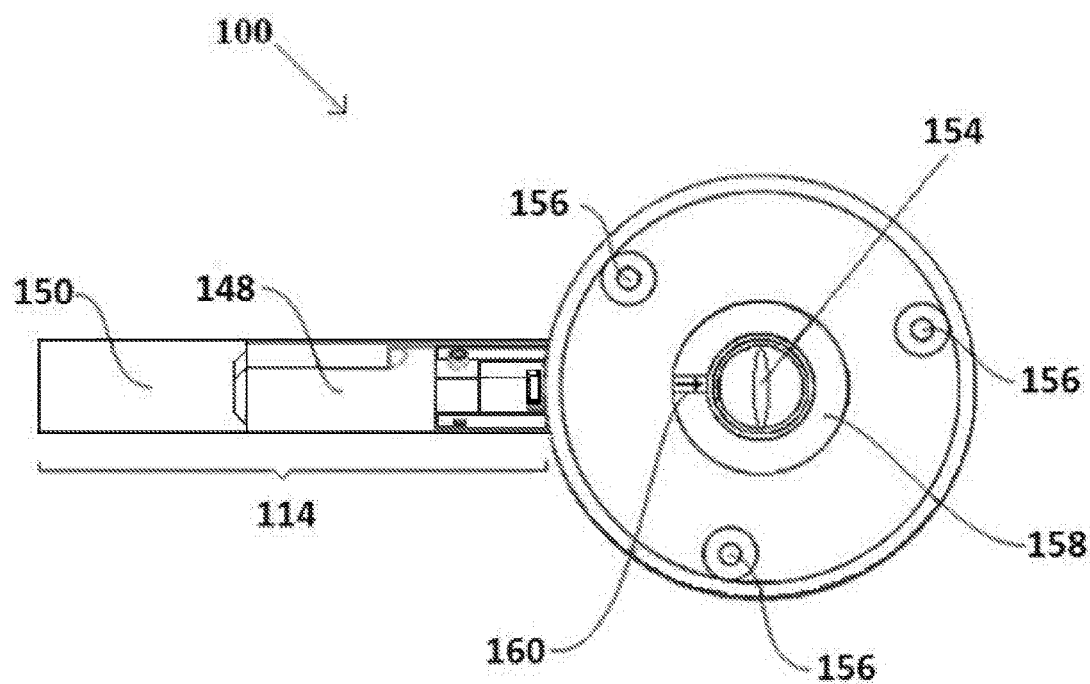
FIG. 4 provides a top plan view of the laparoscopic head single loader of FIG. 3, showing an indicator used for proper orientation.

With respect to FIG. 4 a top perspective view of the laparoscopic single loader device (100) is illustrated. A top lumen passageway seal (154) is illustrated in its closed position. Three funnel attachment screws (156) are used to secure the top section to the rest of the device. A unique instrument pen cap orientation indicator (160) is used to indicate the proper orientation of the instrument shaft (152). This is important because once the laparoscopic single loader device (100) is inserted into the abdomen (176 of FIG. 3) the orientation of the instrument pen cap device (114) cannot be visually ascertained. An instrument shaft (152) needs to enter the pen cap device from the direction of the instrument pen cap orientation indicator (160).

Figure 5:
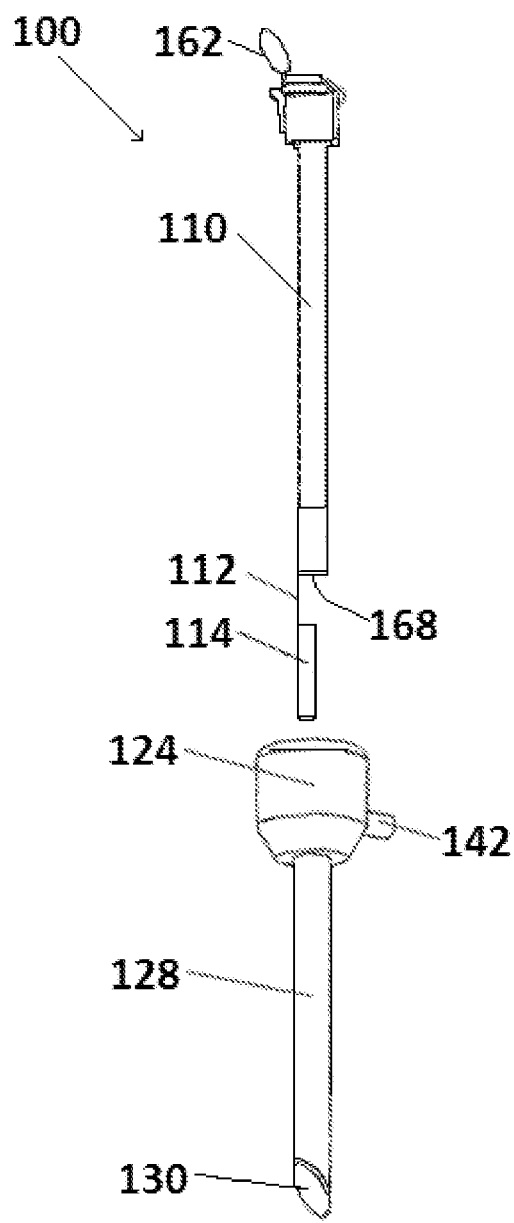
FIG. 5 provides a perspective view of a laparoscopic head single loader according to an alternative embodiment, and shown being inserted into a trocar.

With respect to FIG. 5 a perspective view of an alternative embodiment of the laparoscopic single loader device (100) is illustrated having a tab guide (162) used for controlling the instrument pen cap device (114). The tab guide (162) uses a pen cap wire (112) running along the longitudinal axis of the delivery tube (110) protruding through the distal end (168) and to the instrument pen cap device (114). The device is prepared for use by then inserting it into a trocar (124).

Figure 6:
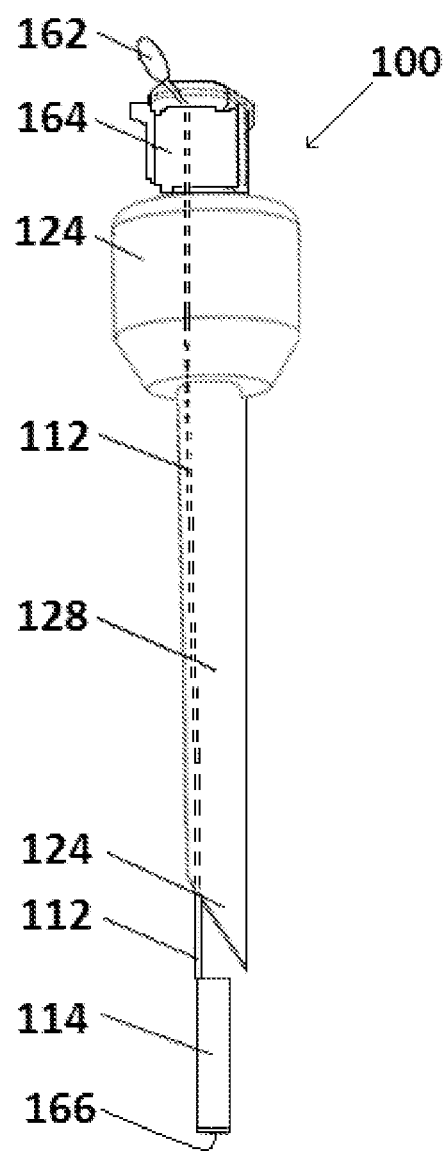
FIG. 6 provides a perspective view of the laparoscopic head single loader of FIG. 5, shown inserted into a trocar device.

With respect to FIG. 6 a perspective view of the laparoscopic single loader device (100) is illustrated fully inserted into a trocar device (124) prior to having the instrument pen cap device changing its attachment orientation position.

Figure 7:
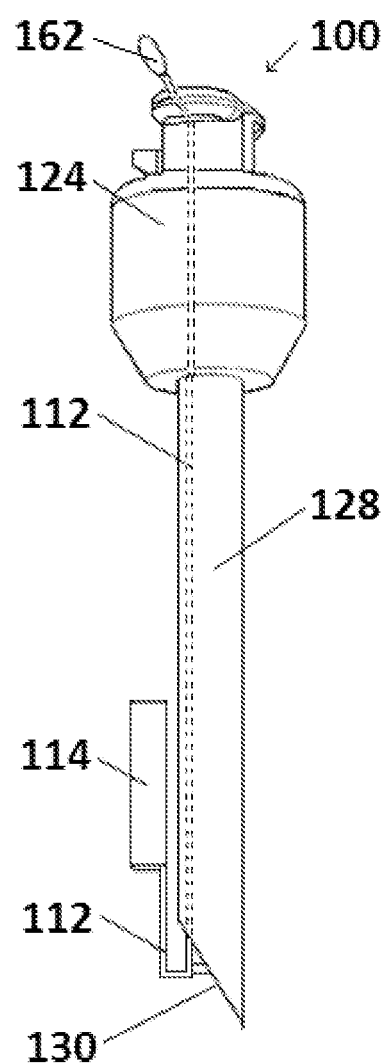
FIG. 7 provides a perspective view of the laparoscopic head single loader of FIG. 5, showing an instrument pen cap device in proper orientation parallel to a trocar lumen.

With respect to FIG. 7 a perspective view of the laparoscopic single loader device (100) is illustrated having the instrument pen cap device (114) properly oriented in parallel to the trocar lumen (128). The pen cap attachment wire (112) is used to place the instrument pen cap device into its proper orientation.

Figure 8A:
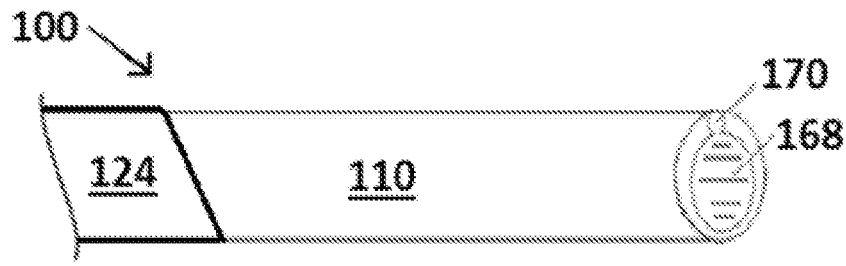
FIG. 8A provides a perspective view of a distal end portion of the laparoscopic head single loader.
Figure 8B:
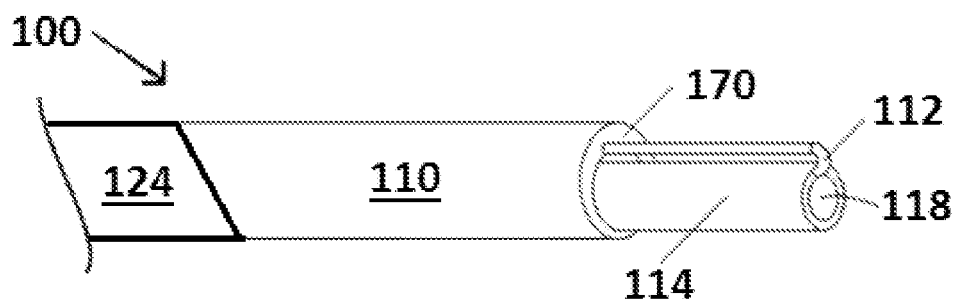
FIG. 8B provides a perspective view of the alternative instrument head extending through the insertion device.
Figure 8C:
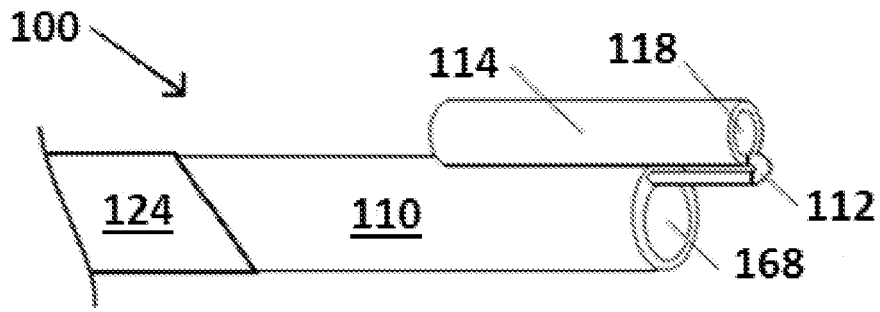
FIG. 8C provides a perspective view of the distal end portion of the laparoscopic head single loader shown bending to its memory metal position.

With respect to FIGS. 8A-8C an attachment wire lumen (170) is illustrated at the distal end of the laparoscopic single loader device (100). The attachment wire lumen (170) is used to guide pen cap attachment wire (112) through the delivery tube (110). In FIG. 8B the instrument pen cap device (114) begins protruding at the distal end (168) of the laparoscopic single loader device (100). Once the instrument pen cap device (114) is fully exposed it is turned around to the external side of the delivery tube (100). This can take place by having the pen cap attachment wire (112) made out of memory metal material or prefabricated wire. By bending the instrument pen cap device out of the distal end (168) a laparoscope (136 of FIG. 3) can be used to maintain direct visualization of the attachment procedure.

Figure 9:
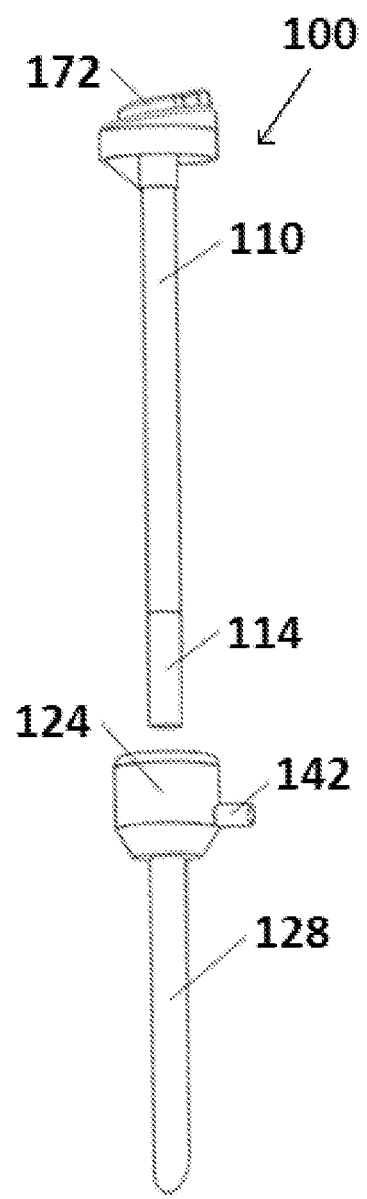
FIG. 9 provides a perspective view of an alternative laparoscopic instrument head single loader device prior to insertion into a trocar.

With respect to FIG. 9 a perspective view of an alternative embodiment of the laparoscopic single loader device (100) is illustrated using a circular latch (172) at the laparoscopic single loader proximal end used to move the instrument pen cap (114) radially outward once correctly inserted into trocar (124).

Figure 10:
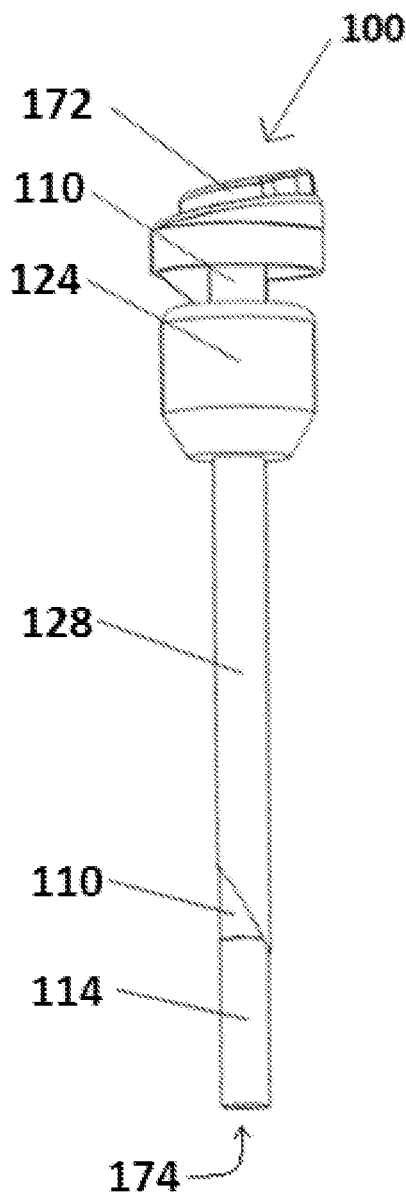
FIG. 10 provides a perspective view of the laparoscopic instrument head single loader of FIG. 9, shown fully inserted in its preposition state.

With respect to FIG. 10 a perspective view of the laparoscopic single loader device (100) is illustrated fully inserted into trocar device (124). When the instrument pen cap device (114) reaches the end of the trocar lumen (128) it is correctly oriented and ready for use.

Figure 11:
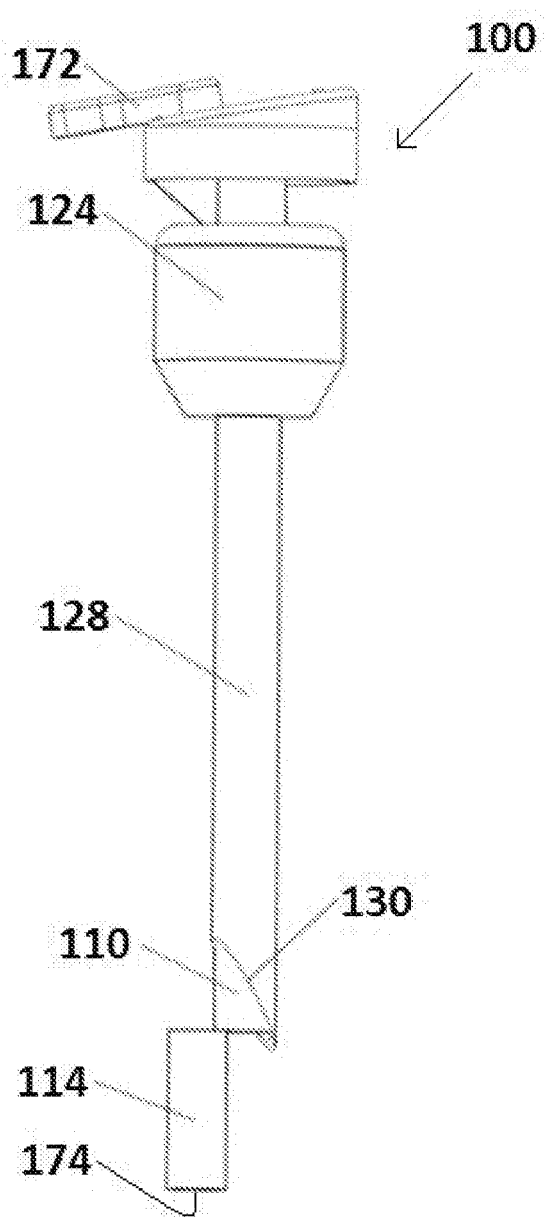
FIG. 11 provides a perspective view of the laparoscopic instrument head single loader FIG. 9, shown fully inserted in its preposition state and positioned for deployment.

With respect to FIG. 11 a perspective view of the laparoscopic single loader device (100) is illustrated properly deployed. Circular latch (172) is turned outwardly at the proximal end of the laparoscopic single loader device (100). When the circular latch (172) is rotated an attachment wire (112) not shown also rotates causing the instrument pen cap device (114) to rotate outwardly clearing the passage way of the delivery tube (110).

In an embodiment, a single instrument head loading device for use in needlescopic surgery is provided. The single device includes a shaft having maneuverable structure on a proximal end thereof for use in correctly positioning an instrument head at a distal end thereof through manipulation of at least one wire engaged to a distal end loader within which the instrument head is held by maneuvering the maneuverable structure at the proximal end, to which a proximal end of the at least one wire is attached, the at least one wire traversing the length of the shaft and the distal end loader being positioned in a suitable position for allowing engagement of the instrument head under continuous direct visualization to a distal end of a cooperating shaft of a surgical instrument as well as allowing for disengagement of the instrument head back into the distal end loader under continuous direct visualization, the engagement and disengagement taking place within a body cavity.

Furthermore, in an embodiment, the maneuverable structure on the proximal end of the shaft of the device may be of any suitable configuration allowing for maneuvering of the instrument head to the suitable position for engagement to or disengagement from the distal end of the cooperating surgical instrument shaft under continuous direct visualization within the body cavity.

In an embodiment, the at least one wire traversing the length of the device shaft is received within a canal therefor along an interior surface of the device shaft. In an embodiment, the at least one wire traversing the length of the device shaft runs along an interior surface of the device shaft. In an embodiment, the instrument head is covered by a pen cap type structure. In yet another embodiment, the instrument head is uncovered.

The instrument head single loader allows for the continuous direct visualization of instrument head attachment by providing by a surgical scope inserted through the device shaft into the body cavity. In an embodiment, the wire is preset to any suitable angle up to 180 degrees from its original position coaxial with an axis of the shaft of the device. In an embodiment the instrument head may be selected from the group comprising, though not limited to, scrapers, graspers, Maryland dissectors, claw forceps, fenestrated grasping forceps, electrodes, or tapered grasping forceps. Other instrument heads may also be utilized with the instrument head single loader without departing from the broader aspects of the invention.

In an embodiment, the instrument head is sized for laparoscopic surgery. In an embodiment, the instrument head is configured to engage to a distal end of a needlescopic device. In an embodiment, the instrument loader is engaged to the maneuvering structure by more than one wire. The at least one wire may be made of memory metal or a preshaped metal. In an embodiment, the radial position of the instrument head loader is indicated by visual indicia along the proximal end of the device.

In an embodiment, the pen cap of the instrument head single loader is manipulated by at least one wire engaged between the pen cap and a manual handle located on the proximal end of the device shaft. The wire engaged to the pen cap traverses the length of the device shaft within a channel therefor to maintain the pen cap in a proper orientation. The instrument head single loader may also include a tab-controlled seal element to maintain body cavity inflation during use. The instrument head single loader may include a positioning tab provided on the distal end of the loader which engages within a slot for same in the distal end of the device shaft. In an embodiment, the wire is replaced by a pivot hinge which is preset to a particular angle relative to the device shaft.

Although this invention has been shown and described with respect to the detailed embodiments thereof, it will be understood by those of skill in the art that various changes may be made and equivalents may be substituted for elements thereof without departing from the scope of the invention. In addition, modifications may be made to adapt a particular situation or material to the teachings of the invention without departing from the essential scope thereof. Therefore, it is intended that the invention not be limited to the particular embodiments disclosed in the above detailed description, but that the invention will include all embodiments falling within the scope of this disclosure.

What is claimed is:

1. A instrument head loading device, comprising:
   a hollow shaft having a longitudinal axis; and
   a distal end loader configured to receive an instrument head for delivery into a body cavity, the distal end loader having a longitudinal extent and being movable between a first position where the longitudinal extent of the distal end loader is generally parallel to the longitudinal axis of the hollow shaft, and a second position where the longitudinal extent of the distal end loader is generally perpendicular to the longitudinal axis of the hollow shaft to expose the instrument head to a distal end of a cooperating shaft of a surgical instrument within the body cavity;
   wherein the hollow shaft is configured to receive a visualization device therethrough, allowing for engagement of the instrument head to the distal end of the cooperating shaft under continuous direct visualization.

2. The device of claim 1 wherein the distal end loader is received at a distal end of the hollow shaft and is pivotable with respect to the hollow shaft.

3. The device of claim 2 wherein the distal end loader is manipulated by at least one wire engaged between the pen cap distal end loader and a manual handle located on the proximal end of the device shaft.

4. The device of claim 2 wherein the wire engaged to the distal end loader traverses the length of the device shaft within a channel therefor to maintain the distal end loader in a proper orientation.

5. The device of claim 1 wherein the instrument head is uncovered.

6. The device of claim 1 wherein the visualization device is a surgical scope inserted through the hollow shaft into the body cavity.

7. The device of claim 1 wherein the instrument head is selected from the group comprising, though not limited to, scrapers, graspers, Maryland dissectors, claw forceps, fenestrated grasping forceps, electrodes, or tapered grasping forceps.

8. The device of claim 1 wherein the instrument head is sized for laparoscopic surgery.

9. The device of claim 1 wherein the instrument head is configured to engage to a distal end of a needlescopic device.

10. The device of claim 1 wherein a radial position of the distal end loader is indicated by visual indicia along the proximal end of the device.

11. The device of claim 1 further comprising:
    a tab controlled seal element to maintain body cavity inflation during use.

12. The device of claim 1 wherein a positioning tab is provided on the distal end loader which engages within a slot for same in the distal end of the device shaft.

13. The device of claim 1 wherein the distal end loader includes a pivot hinge which is preset to a particular angle relative to the hollow shaft for moving the distal end loader from the first position to the second position when the distal end loader is extended from a distal end of the hollow shaft.

14. The device of claim 1, wherein:
    the distal end loader is coupled to a maneuverable structure on a proximal end of the device via at least one wire;
    wherein the maneuverable structure is operable to move the distal end loader between the first position and the second position through manipulation of the at least one wire.

15. The device of claim 14 wherein the maneuverable structure on the proximal end of the shaft of the device allows for maneuvering of the instrument head to a suitable position for engagement to or disengagement from the distal end of the cooperating surgical instrument shaft under continuous direct visualization within the body cavity.

16. The device of claim 14 wherein the at least one wire extends the length of the device shaft and is received within a canal therefor along an interior surface of the device shaft.

17. The device of claim 14 wherein the at least one wire extends the length of the device shaft runs along an interior surface of the device shaft.

18. The device of claim 14 wherein the wire is preset to any suitable angle up to 180 degrees from its original position coaxial with an axis of the shaft of the device.

19. The device of claim 14 wherein the instrument loader is engaged to the maneuvering structure by more than one wire.

20. The device of claim 14 wherein the at least one wire is made of memory metal.

21. The device of claim 14 wherein the at least one wire is made of preshaped metal.

* * * * *